United States Patent
Margulies (10) Patent No.: US 12,109,226 B1
(45) Date of Patent: Oct. 8, 2024

(54) POLYSILANE METHACRYLIC COMPOUNDS AND METHODS OF MAKING THEM

(71) Applicant: Zetagen Therapeutics, Inc., Syracuse, NY (US)

(72) Inventor: Bryan S. Margulies, Liverpool, NY (US)

(73) Assignee: Zetagen Therapeutics, Inc., Syracuse, NY (US)

( * ) Notice: Subject to any disclaimer, the term of this patent is extended or adjusted under 35 U.S.C. 154(b) by 0 days.

(21) Appl. No.: 18/634,556

(22) Filed: Apr. 12, 2024

Related U.S. Application Data (60) Provisional application No. 63/549,854, filed on Feb. 5, 2024.

(51) Int. Cl.
*A61K 31/80* (2006.01)
*A61K 31/485* (2006.01)
*A61L 27/16* (2006.01)
*C08F 230/08* (2006.01)

(52) U.S. Cl.
CPC ............ *A61K 31/80* (2013.01); *A61K 31/485* (2013.01); *A61L 27/16* (2013.01); *C08F 230/085* (2020.02); *A61L 2300/204* (2013.01); *A61L 2430/02* (2013.01); *C08F 2810/30* (2013.01)

(58) Field of Classification Search
None
See application file for complete search history.

(56) References Cited

U.S. PATENT DOCUMENTS

2010/0015441 A1\* 1/2010 Zhao ................... C10M 155/02
556/439

\* cited by examiner

*Primary Examiner* — Brian Gulledge
(74) *Attorney, Agent, or Firm* — Foley & Lardner LLP (57) ABSTRACT

A polysilane methacrylic polymer and processes of preparing the polysilane methacrylic polymer are provided.

12 Claims, 5 Drawing Sheets

FIG. 1

|   | Name  | Shift | Integral | Class | J's                |
|---|-------|-------|----------|-------|--------------------|
| 1 | A (s) | 3.57  | 9.93     | s     |                    |
| 2 | B (d) | 1.93  | 1.01     | d     | 12.26              |
| 3 | C (q) | 1.86  | 1.15     | q     | 12.79, 12.79, 12.28 |
| 4 | D (s) | 1.79  | 3.09     | s     |                    |
| 5 | E (t) | 1.41  | 0.88     | t     | 14.84, 14.84       |
| 6 | G (d) | 0.81  | 6.14     | d     | 8.86               |
| 7 | H (s) | 7.26  | 0.08     | s     |                    |

|   | Name | Shift | Integral | Class | J's |
|---|------|-------|----------|-------|-----|
| 1 | B (s) | 177.99 | 0.20 | s | |
| 2 | G (s) | 54.28 | 1.76 | s | |
| 3 | J (s) | 51.67 | 2.12 | s | |
| 4 | N (s) | 44.74 | 1.71 | s | |
| 5 | P (s) | 29.53 | 0.14 | s | |
| 6 | R (s) | 18.57 | 2.17 | s | |
| 7 | S (s) | 16.32 | 4.05 | s | |

POLYSILANE METHACRYLIC COMPOUNDS AND METHODS OF MAKING THEM

CROSS-REFERENCE TO RELATED APPLICATIONS

This application claims the benefit of priority to U.S. Provisional Patent Application No. 63/549,854, filed on Feb. 5, 2024, the contents of which are incorporated herein by reference in their entirety.

FIELD

The present invention relates to a process for the preparation of a polysilane methacrylic compounds and polymers formed with them, as well as the products and uses resulting from their application.

SUMMARY

One aspect of the present invention provides a compound of formula (I):

wherein each of $R^1$, $R^2$, $R^3$, $R^4$, $R^5$, $R^6$, and $R^7$ is independently selected from the group consisting of H, alkyl, alkenyl, alkoxy, aryl, aralkyl, cycloalkyl, heterocyclyl, heteroaryl groups, hydroxyl, or halo, and wherein n is independently for each occurrence an integer from 1 to 1000000.

Another aspect of the present invention provides a compound having a formula (Ia):

wherein n is independently for each occurrence an integer from 1 to 1000000.

Another aspect of the present invention provides a compound having a formula (II):

wherein n is independently for each occurrence an integer from 1 to 1000000.

Another aspect of the present invention provides a compound having a formula (III):

where $R^1$, $R^2$, and $R^3$ are each independently selected from the group consisting of H, alkyl, alkenyl, alkoxy, aryl, aralkyl, cycloalkyl, heterocyclyl, heteroaryl groups, hydroxyl, or halo, and n is independently for each occurrence an integer from 1 to 1000000.

Another aspect of the present invention provides a compound having a formula (IV):

wherein each of $R^1$, $R^2$, $R^3$, $R^4$, $R^5$, $R^6$, and $R^7$ is selected from the group consisting of H, alkyl, alkenyl, alkoxy, aryl, aralkyl, cycloalkyl, heterocyclyl, heteroaryl groups, hydroxyl, or halo, and wherein n is independently for each occurrence an integer from 1 to 1000000.

Another aspect of the present invention provides a compound having a formula (IVa):

(IVa)

wherein n is independently for each occurrence an integer from 1 to 1000000.

Another aspect of the present invention provides a method of preparing a polysilane methacrylic compound, the method comprising: a) reacting methyl methacrylate with tetraethyl orthosilicate and 1,1,3,3-tetramethyldisilane to form the polysilane methacrylic compound.

Another aspect of the present invention provides a method of preparing $SiH_3-[SiH_2]_n-SiH_2-[C_5H_7O_2]_n$, the method comprising: reacting methyl methacrylate with tetraethyl orthosilicate and 1,1,3,3-tetramethyldisilane to form the $SiH_3-[SiH_2]_n-SiH_2-[C_5H_7O_2]_n$, wherein n is independently for each occurrence an integer from 1 to 1000000.

Another aspect of the present invention provides a polymer comprising any one of the compounds having the formula (I), (Ia), (II), (III), (IV), or (IVa).

FIGURES

FIG. 5 shows how the annealing process incorporates a calcium salt into the compound.

DETAILED DESCRIPTION

The following patent documents, each of which is incorporated herein by reference, may be useful for understanding this disclosure: PCT patent application publications Nos. WO2021/011529; WO2022/015364; U.S. patent application publications Nos. 2019-0093109; 2021-0030746; 2021-0228571; 2022-0016312; U.S. Pat. No. 11,471,454.

As used in this disclosure and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "analog" refers to a compound in which one or more individual atoms or functional groups have been replaced, either with a different atom or a different functional group, generally giving rise to a compound with similar properties. In some aspect, the analog refers to a structure that is similar to another but differs in one or two components.

The term "derivative" refers to a compound that is formed from a similar beginning compound by attaching another molecule or atom to the beginning compound. Further, derivatives, according to the invention, encompass one or more compounds formed from a precursor compound through addition of one or more atoms or molecules or through combining two or more precursor compounds.

An "alkyl" group is a saturated, partially saturated, or unsaturated straight chain or branched non-cyclic hydrocarbon having from 1 to 20 carbon atoms. Representative alkyl groups include-methyl,-ethyl,-n-propyl,-n-butyl,-n-pentyl and -n-hexyl; while saturated branched alkyls include-isopropyl,-sec-butyl,-isobutyl,-tert-butyl,-isopentyl,-neopentyl, tert-pentyl, -2-methylpentyl,-3-methylpentyl,-4-methylpentyl,-2,3-dimethylbutyl and the like. An alkyl group can be substituted or unsubstituted.

An "alkenyl" group is a straight chain or branched non-cyclic hydrocarbon having from 2 to 20 carbon atoms. Representative straight chain and branched alkenyls include-vinyl,-allyl, -1-butenyl,-2-butenyl,-isobutylenyl,-1-pentenyl, 2pentenyl,-3-methyl-1-butenyl,-2-methyl-2-butenyl,-2,3-dimethyl-2-butenyl,-1-hexenyl, 2-hexenyl,-3-hexenyl,-1-heptenyl,-2-heptenyl,-3-heptenyl,-1-octenyl,-2-octenyl, 3octenyl and the like. The double bond of an alkenyl group can be unconjugated or conjugated to another unsaturated group. An alkenyl group can be unsubstituted or substituted.

A "cycloalkyl" group is a saturated, partially saturated, or unsaturated cyclic alkyl group of from 3 to 20 carbon atoms having a single cyclic ring. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

A "heterocyclyl" is an aromatic (also referred to as heteroaryl) or non-aromatic cycloalkyl in which at least one of the ring carbon atoms are independently replaced with a heteroatom from the group consisting of O, S and N. In some embodiments, heterocyclyl groups include 3 to 20 ring members. Heterocyclyls can also be bonded to other groups at any ring atom (i.e., at any carbon atom or heteroatom of the heterocyclic ring). A heterocyclyl group can be substituted or unsubstituted.

An "aryl" group is a fully aromatic carbocyclic group of from 6 to 20 carbon atoms having a single ring (e.g., phenyl). Particular aryls include phenyl, biphenyl, naphthyl and the like. An aryl group can be substituted or unsubstituted.

A "heteroaryl" group is an aryl ring system having one or more heteroatoms as ring atoms in a heteroaromatic ring system, wherein the remainder of the atoms are carbon atoms. In some embodiments, heteroaryl groups contain 3 to 20 ring atoms. Suitable heteroatoms include oxygen, sulfur, and nitrogen.

An "alkoxy" or "alkoxyl" group is —O— (alkyl), wherein alkyl is defined above.

An "aralkyl" group is a radical of the formula:-alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups.

A "halogen" is fluorine, chlorine, bromine or iodine.

When the groups described herein are said to be "substituted," they may be substituted with any appropriate substituent or substituents. Illustrative examples of substituents include, but are not limited to, halogen (chloro, iodo, bromo, or fluoro); alkyl; alkenyl; alkynyl; hydroxyl; alkoxy; alkoxyalkyl; amino; alkylamino; carboxy; nitro; cyano; thiol; thioether; imine; imide; thiocarbonyl; sulfonyl; sulfone; sulfonamide; ketone; aldehyde; ester; cycloalkyl; heterocyclyl; aryl; aralkyl; aryloxy; aralkyloxy; heterocyclyloxy; and heterocyclyl alkoxy.

As used herein, the term "substituent" refers to an atom or a group of atoms replacing a hydrogen atom on the parent molecule. The term "optionally substituted" means that the specified group is unsubstituted or substituted by one or more substituents, independently chosen from the group of possible substituents. When indicating the number of substituents, the term "one or more" refers to a range from one substituent to the highest possible number of substituents, i.e., replacement of from one hydrogen up to replacement of all hydrogen atoms by substituents, for example, 1 to 8, 1 to 7, 1 to 6, 1 to 5, 1 to 4, 1 to 3, 1 or 2, or one substituents. And it will be understood by those skilled in the art with respect to any chemical group containing one or more substituents that such groups are not intended to introduce any substitution or substitution patterns that are sterically impractical and/or physically non-feasible.

Organic silicon-based chemicals are a class of materials that can be used to form polymers.

In one aspect, provided is a new silicon-based organic compound comprising a novel structure as shown by the following Formula (I):

(I)

where each of $R^1$, $R^2$, $R^3$, $R^4$, $R^5$, $R^6$, and $R^7$ is independently selected from the group consisting of H, alkyl, alkenyl, alkoxy, aryl, aralkyl, cycloalkyl, heterocyclyl, heteroaryl groups, hydroxyl, or halo.

In another aspect, provided is a silicon-based organic compound comprising a novel structure as shown by the following Formula (Ia):

(Ia)

In another aspect, provided is a compound of Formula (II):

(II)

which is similar to the compound of Formula (Ia), but the molecule is capped with a dimethyl silane.

In yet another aspect, provided is a compound of Formula (III):

(III)

which is similar to the compound of Formula (I), but the molecule is capped with a silane, where $R^1$, $R^2$, and $R_3$ are each independently selected from the group consisting of H, alkyl, alkenyl, alkoxy, aryl, aralkyl, cycloalkyl, heterocyclyl, heteroaryl groups, hydroxyl, or halo.

In another aspect, provided is a compound of Formula (IV):

(IV)

wherein each of $R^1$, $R^2$, $R^3$, $R^4$, $R^5$, $R^6$, and $R^7$ is selected from the group consisting of H, alkyl, alkenyl, alkoxy, aryl, aralkyl, cycloalkyl, heterocyclyl, heteroaryl groups, hydroxyl, or halo. Compound (IV) is similar to the compound of Formula (I), but has a calcium phosphate group (e.g., $Ca_3(PO_4)_2$) added.

In another aspect, provided is a compound of Formula (IVa):

(IVa)

In any of the embodiments described herein, n is an integer from 1 to 1000000, or any range including and between any two of these values. The value "n" may be any integer from 1 to 1000000. As used herein, "n" is a repeating unit that represents the number of repeating monomer units that are within a macro-molecule. As an example, when n=1, the compound is a monomer; when n=2, the compound is a dimer; when n=3, the compound is a trimer, etc.

In an aspect, provided is a polymer comprising any one of the compounds of Formula (I, Ia, II, III, IV, or IVa).

In some embodiments, the polymer is a small molecular weight polymer, wherein n is from 1 to 100, or any range including and between any two of these values. For a small molecular weight polymer, n may be any integer from 1 to 100. For example, in some embodiments, n may be 1, 2, 3, 4, 5, 6, 7, 8, 9, or 10. As another example, n may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, the polymer is a medium to large molecular weight polymer, wherein n is from 101 to 1000, from 101 to 10000, from 101 to 100000, or from 101 to 1000000, or any range including and between any of these values. For a medium to large molecular weight polymer, n may be any integer from 101 to 1000000. For example, in some embodiments, n may be 1000, 1010, 1020, 1030, 1040, 1050, 1060, 1070, 1080, 1090, 1100, 1200, 1300, 1400, 1500, 1600, 1700, 1800, 1900, 2000, 4000, 5000, 6000, 7000, 8000, 9000, 10000, 20000, 30000, 40000, 50000, 60000, 70000, 80000, 90000, or 100000. As another example, n may be 242, 338, 450, 577, 603, 720, 810, 909, 1001, 1066, 1233, 1342, 1450, 1502, 1620, 1793, 1888, 1907, 1910, 1914, 1916, 1942, 1945, 1953, 1954, 1976, 1978, 1979, 1980, 1983, 1984, 1986, 1994, 1996, 2004, 2012, 2014, 2016, 3030, 4444, 5050, 6060, 7777, 8210, 9009, 10560, 20234, 30201, 44204, 50310, 62091, 72000, 81000, 99999, 100010, 111116, 999000, 1072040, or 2030405.

In an aspect, provided are methods of making the compound of Formula (I), (Ia), (II), (III), (IV), or (IVa). The methods may include standard chemical processes.

In an exemplary embodiment, a method of making a compound of Formula (Ia) comprises reacting tetraethyl orthosilicate with 1,1,3,3-tetramethyldisilane and polymethyl methacrylate, which is described herein in greater detail as Scheme 1:

Scheme 1:

Scheme 1 starts with methyl methacrylate (CAS #9011-14-7), $C_5H_8O_2$. To 1-g of methyl methacrylate, 0.375-mL of tetraethyl orthosilicate (TEOS) $SiC_8H_{20}O_4$ and 0.375-mL of 1,1,3,3-tetramethyldisilane (TMDS) $[(CH_3)_2SiH]_2O$ are added. At room temperature (25° C.) the mixture undergoes an endothermic reaction, reaching a reaction temperature of approximately 20° C. After 10-minutes the mixture becomes a white, viscous powder material. After 12- to 18-hours the viscous properties are lost, and the white material is a fine granular powder. Heating at normal pressure or under vacuum do not accelerate this process. Heating the final product to 60° C. for 1-hour causes the excess ethanol and water to evaporate, thus drying the product.

Figure 1:
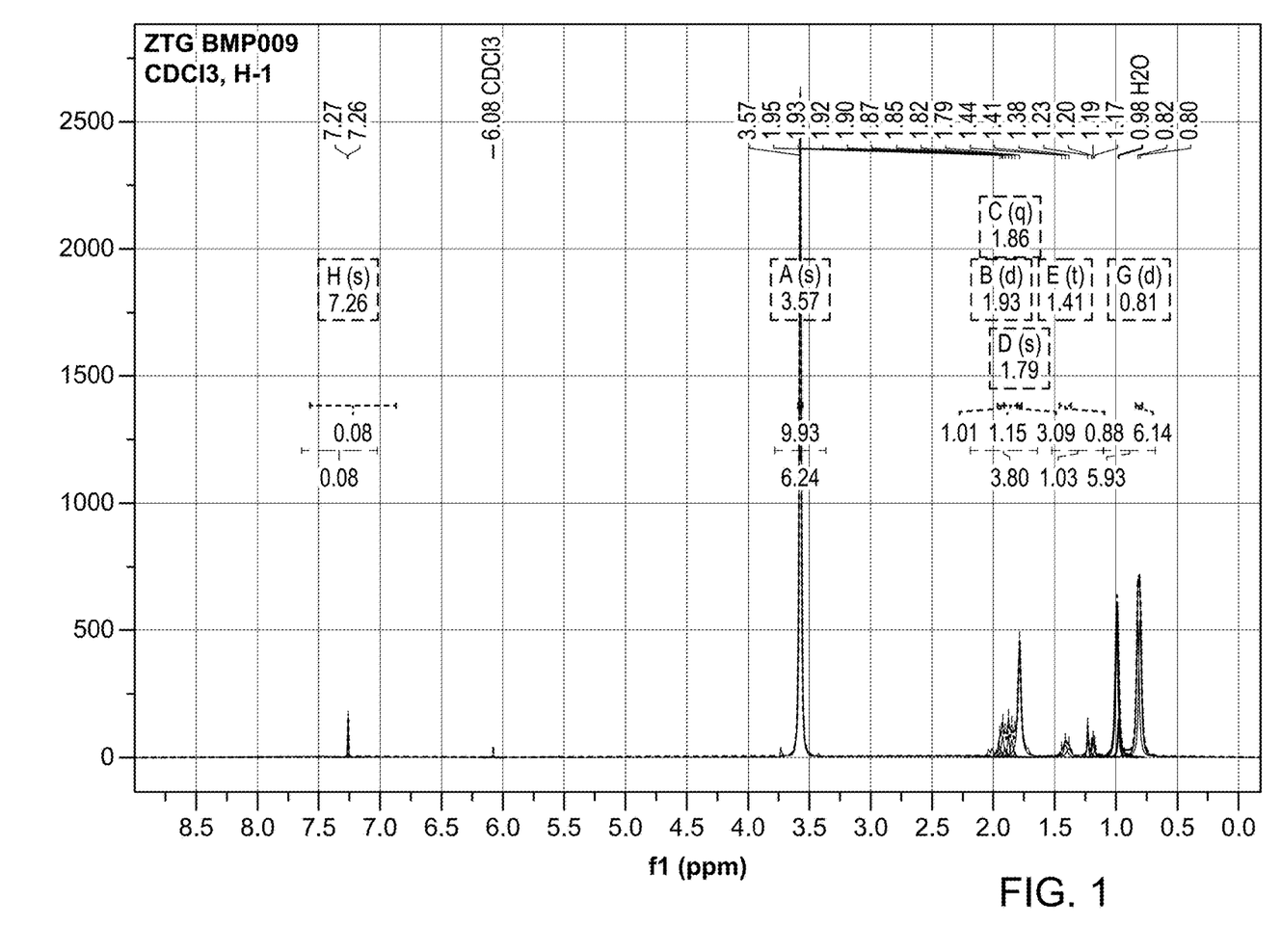
FIG. 1 shows the $H^1$ NMR spectrum of the compound of Formula (Ia).
Figure 2:
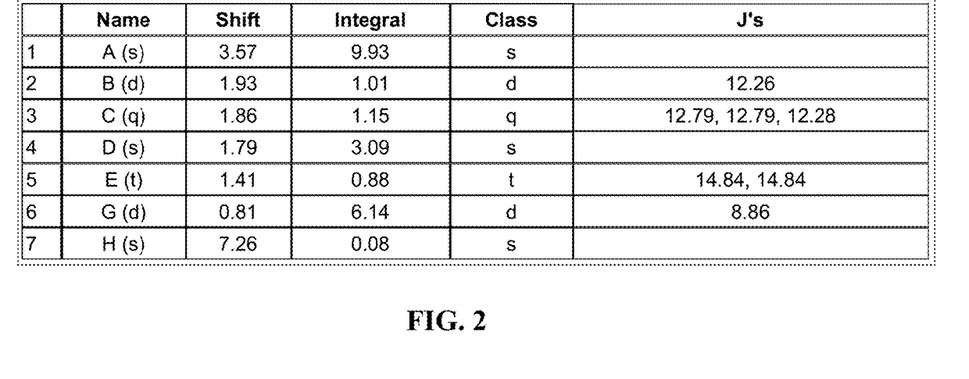
FIG. 2 shows the results of the Peaks, Multiplet, and Integral Analyses for the $H^1$ NMR spectrum of FIG. 1.
Figure 3:
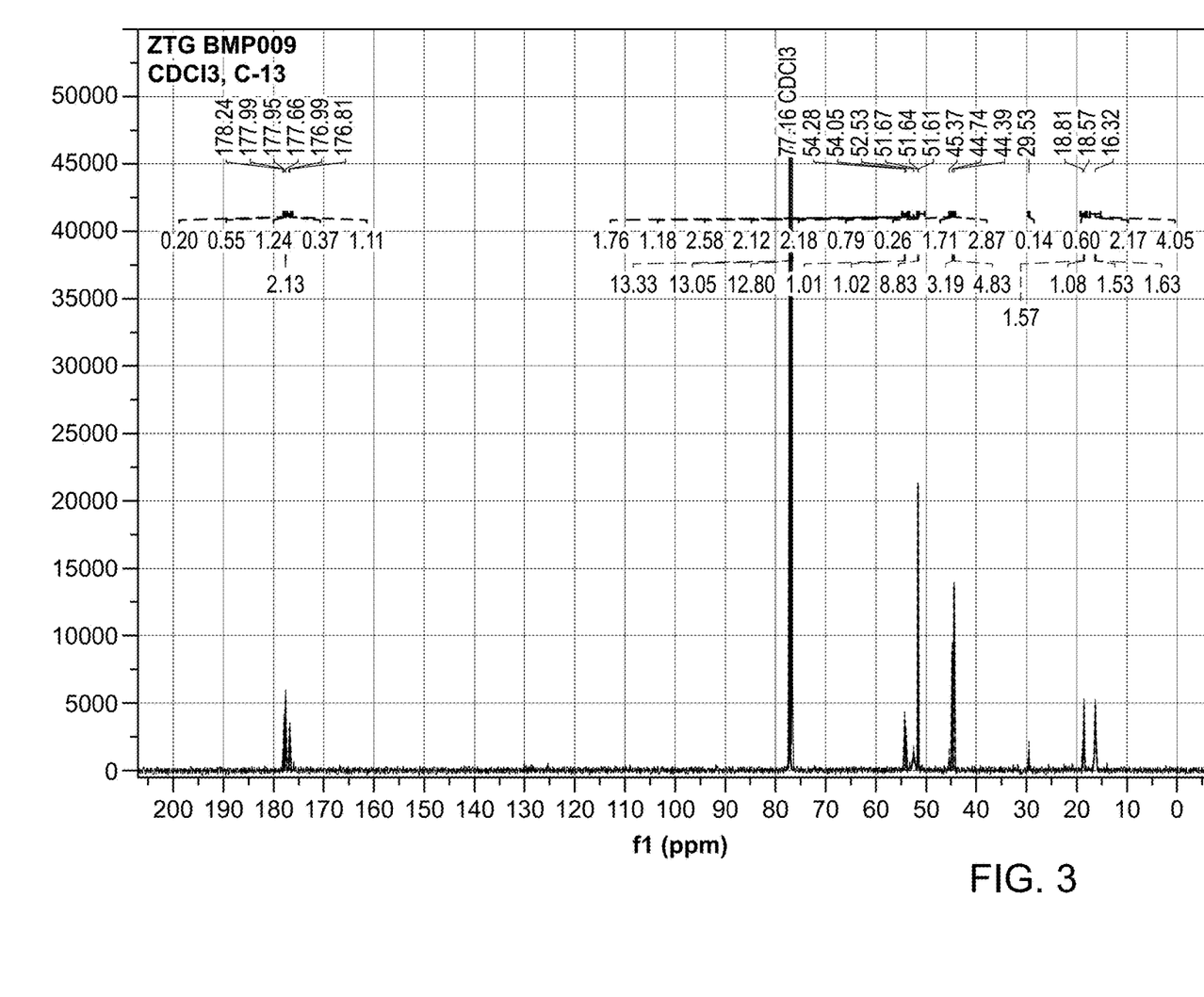
FIG. 3 shows the $C^{13}$ NMR spectrum of the compound of Formula (Ia).
Figure 4:
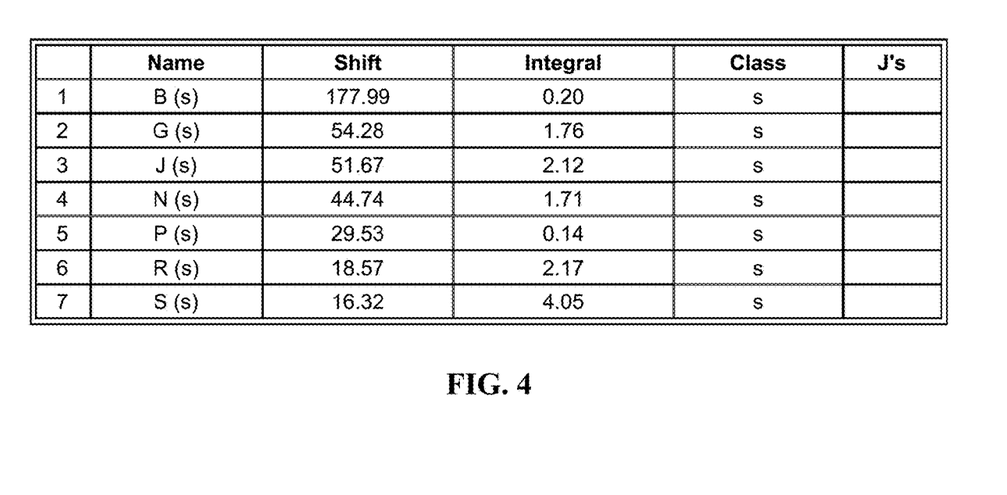
FIG. 4 shows the results of the Peaks, Multiplet, and Integral Analyses for the $C^{13}$ NMR spectrum of FIG. 3.
Figure 5:
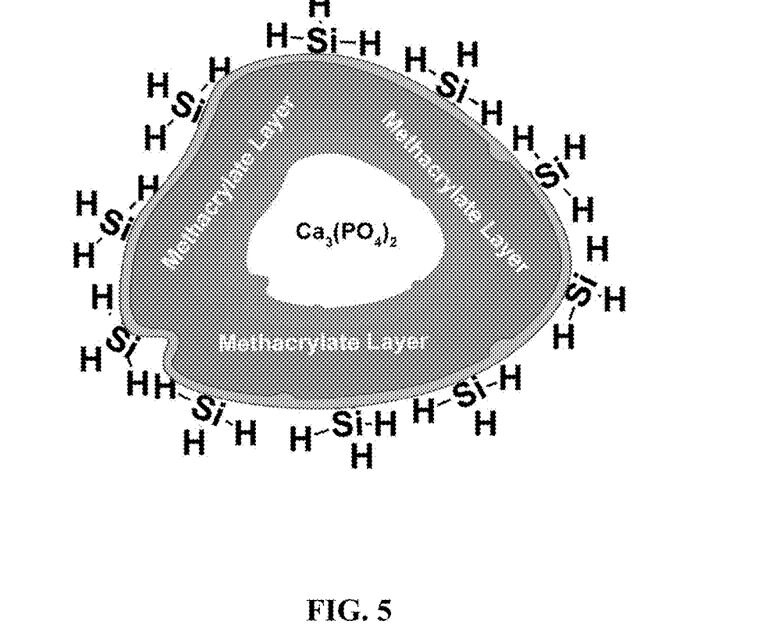
FIG. 5 shows a representative image of the molecular shape of a compound of Formula (IVa) which comprises a calcium phosphate group.

Another exemplary embodiment includes methods of making a compound of Formula (IVa). These methods can be accomplished, for example, through a novel chemical process, in which the addition of a calcium phosphate salt, $Ca_{10}(PO_4)_6(OH)_2$ is added to $SiH_3$—$[SiH_2]_n$—$SiH_2$—$[C_5H_7O_2]_n$ via an annealing process. Annealing in this case involves using heat to open the $SiH_3$—$[SiH_2]_n$—$SiH_2$—$[C_5H_7O_2]_n$ molecule, allowing the $Ca_{10}(PO_4)_6(OH)_2$ salt to bind via static forces with methacrylate center (FIG. 5).

Another aspect provides a method of making a polymer from any one of the compounds of Formula (I, Ia, II, III, IV, or IVa) via free radical vinyl polymerization.

In an exemplary method, the polymerization is chemically initiated using a Polymerization Initiation Solution, containing the following constituents: The Methyl Anhydride-Glacial Acetic Acid-Ethyl Acetate solution (MAGE) is created by mixing together equal parts of methyl anhydride, glacial acetic acid, and ethyl acetate. To the MAGE solution the Polymerization Initiator Solution is added. The Polymerization Initiator Solution could be composed of any of the following organic polymerization initiators: an initiator, such as azo-bis-isobutyro-nitrile (AIBN), is added alone to the MAGE solution in concentrations between 10% and 60%, including more specifically 10%, 15%, 20%, 25%, 30%, 35%, 40%, 45%, 50%, 55%, or 60%. Even more preference is given to initiator concentrations of 45%, 46%, 47%, 48%, 49%, 50%, 51%, 52%, 53%, 54%, 55%, 56%, and 57%. Additionally, an initiator such as benzoyl peroxide (BPO), can be added alone to the MAGE solution in concentrations between 10% and 60%, including more specifically 10%, 15%, 20%, 25%, 30%, 35%, 40%, 45%, 50%, 55%, or 60%. Even more preference is given to initiator concentrations of 45%, 46%, 47%, 48%, 49%, 50%, 51%, 52%, 53%, 54%, 55%, 56%, and 57%. Additionally, an initiator such as ammonium peroxodisulfate (APS), can be added alone to the MAGE solution in concentrations between 10% and 60%, including more specifically 10%, 15%, 20%, 25%, 30%, 35%, 40%, 45%, 50%, 55%, or 60%. Even more preference is given to initiator concentrations of 45%, 46%, 47%, 48%, 49%, 50%, 51%, 52%, 53%, 54%, 55%, 56%, and 57%. Additionally, an initiator such as Cyclohexyl p-Toluenesulfonate (CPS), can be added alone to the MAGE solution in concentrations between 10% and 60%, including more specifically 10%, 15%, 20%, 25%, 30%, 35%, 40%, 45%, 50%, 55%, or 60%. Even more preference is given to initiator concentrations of 45%, 46%, 47%, 48%, 49%, 50%, 51%, 52%, 53%, 54%, 55%, 56%, and 57%.

Additional polymer initiators could include a mineral acid, including, but not limited to, phosphoric acid, 30% hydrochloric acid, nitric acid, sulfuric, hydrobromic acid, hydroiodic acid, hydrofluoric acid, boric acid, perchloric acid, periodic acid, carbonic acid, chromosulfuric acid, citric acid, fluoroboric acid, formic acid, phosphotungstic acid, acetylsalicylic acid, or butyric acid. Mineral acid Initiators (MAI) can be added alone or in combination with any of the organic polymerization initiators (e.g., AIBN, BPO, APS, or CPS). For instance, AIBN could be combined with phosphoric acid in equal parts. Phosphoric acid could be added to AIBN so that it would constitute one of the following concentration relative to AIBN: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%.

Additional control of polymerization can be achieved using any chemical compound with a central vinyl group (e.g., a vinyl monomer) that includes the following chemical structure ($H_2C=CHR$) and upon polymerization results in an extended alkane chain (e.g., $[-CH_2-CHR-]_n$). The vinyl monomer can be added to the Polymerization Initiation Solution and could include methyl methacrylate, acrylate, ethylene, propene, vinyl chloride, vinyl acetate, vinyl benzoate, acrylonitrile, vinyl chloroacetate, vinyl decanoate, vinyl n-octanoate, vinyl crotonate, vinyl hexanoate, vinyl cinnamate, isobutyl vinyl ether, isoprene vinyl laurate, vinyl pivalate, 1-vinyl-2-pyrrolidone, butyl vinyl ether, vinyl butyrate, ethyl vinyl ether, ethylene glycol monovinyl, vinyl propionate, chloro(methyl)(phenyl)(vinyl)silane, diethyl vinyl phosphonate, trimethyl(vinyloxy)silane, 1,4-bis (dimethyl vinyl silyl) benzene. Vinyl monomer can be added in any of the following percentages to the MAGE-Polymer Initiator Solution: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. Preferred concentrations are 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, and 35%.

The compounds or polymers described herein may further be purified through any standard purification methods. Non-limiting examples of purification methods include recrystallization or chromatography.

The compounds of Formula I, Ia, II, III, IV, or IVa are useful in compositions for treating bone injuries or bone condition, with or without the addition of an active agent, such as an OGFR antagonist. In a preferred embodiment for a composition useful for treating a bone injury or condition, N-allyl noroxymorphone hydrochloride is combined with the compound of Formula I, Ia, II, III, IV, or IVa. The compositions of this embodiment may further be used in accordance with U.S. Pat. No. 10,208,306 or US Patent Application 2022/0016312. In particular, the compounds of Formula I, Ia, II, III, IV, or IVa may be added to any of the compositions of these patents or used to replace the carrier.

The compounds of Formula I, Ia, II, III, IV, or IVa are useful in compositions for treating cancer, with or without the addition of an active agent, such as an OGFR antagonist. In a preferred embodiment for a composition useful for treating cancer, N-allyl noroxymorphone hydrochloride is combined with the compound of Formula I, Ia, II, III, IV, or IVa. The compositions of this embodiment may further be used in accordance with U.S. Pat. No. 11,471,454 or 11,957,676 or U.S. patent application Ser. No. 18/366,439. In particular, the compounds of Formula I, Ia, II, III, IV, or IVa may be added to the compositions of these patents.

EXAMPLES

The following examples further illustrate though in no way limit the present invention.

Example 1—Synthesis of a Compound of Formula (Ia)

The following methods and materials were used to deduce the structure and composition of a compound of Formula (Ia).

$SiH_3-[SiH_2]_n-SiH_2-[C_5H_7O_2]_n$ has a bulk density of 1.006-g/mL. It does not thermally degrade up to temperatures of 1500° C. At 1500° C., the $SiH_3-[SiH_2]_n-SiH_2-[C_5H_7O_2]_n$ material will polymerize into a white dense plastic material. Solubility analysis (Table I) has demonstrated that $SiH_3-[SiH_2]_n-SiH_2-[C_5H_7O_2]_n$ is totally insoluble in aqueous media. It has low solubility in non-aqueous media (e.g., acetone, methanol). $SiH_3-[SiH_2]_n-SiH_2-[C_5H_7O_2]_n$ was found to be most soluble in cyclohexane.

TABLE I

| Diluent | Linear Formula | Solubility: Solubility (10-mg in X-ml) | | Notes |
|---|---|---|---|---|
| | | Volume (mL) | Solubility (mg/mL) | |
| DMSO | $(CH_3)_2SO$ | 6 | 1.67 | |
| Chloroform | $CHCl_3$ | 4 | 2.50 | |
| Dichloromethane | $CH_2Cl_2$ | 3 | 3.33 | |
| Acetonitrile | $C_2H_3N$ | NS | NS | not soluble in 5-mL |

TABLE I-continued

Solubility:
Solubility (10-mg in X-ml)

| Diluent | Linear Formula | Volume (mL) | Solubility (mg/mL) | Notes |
|---|---|---|---|---|
| 1-Propanol | $C_3H_8O$ | 7 | 1.43 | |
| Xylene | $C_8H_{10}$ | 3 | 3.33 | |
| Toluene | $C_6H_5CH_3$ | 3 | 3.33 | |
| Cyclohexane | $C_6H_{12}$ | 2.5 | 4.00 | |
| Acetone | $C_3H_6O$ | NS | NS | not soluble in 20-mL |
| Methanol | $CH_3OH$ | 7 | 1.43 | |

Example 2—Synthesis and Polymerization of a Compound of Formula (IVa)

Compound (IVa) was created by adding equal parts of $SiH_3$—$[SiH_2]_n$—$SiH_2$—$[C_5H_7O_2]_n$ with $Ca_{10}(PO_4)_6(OH)_2$ in a 1:1 ratio. The mixture was then heated to 60° C. for 30-minutes while stirring. This produces a pale blue powder with bulk density of 1.127-grams/mL. The solubility characteristics are the same as the parent $SiH_3$—$[SiH_2]_n$—$SiH_2$—$[C_5H_7O_2]_n$ molecule.

Figure 6:
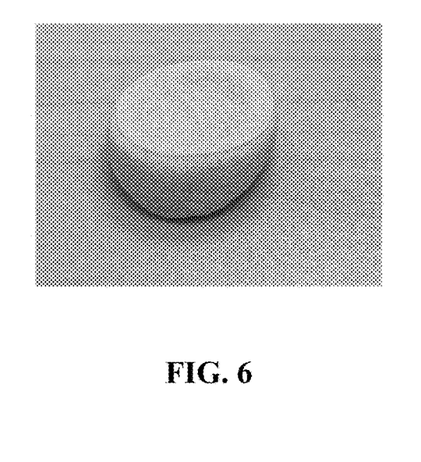
FIG. 6 shows a representative image of a polymerized compound of Formula (IVa).

The MAGE-Polymerization Initiator Solution containing the vinyl monomer methyl methacrylate was added to the $SiH_3$—$[SiH_2]_n$—$SiH_2$—$[C_5H_7O_2]_n$ with $Ca_{10}(PO_4)_6(OH)_2$ (Compound IV) in a ratio of 1:2. Polymerization is isothermic and produces a blue viscous material that polymerizes into a blue material (FIG. 6) within 1-hour. Polymerization can occur in aqueous media, such as water, or in air.

Example 3—Formation of Bone Mineral

Figure 7:
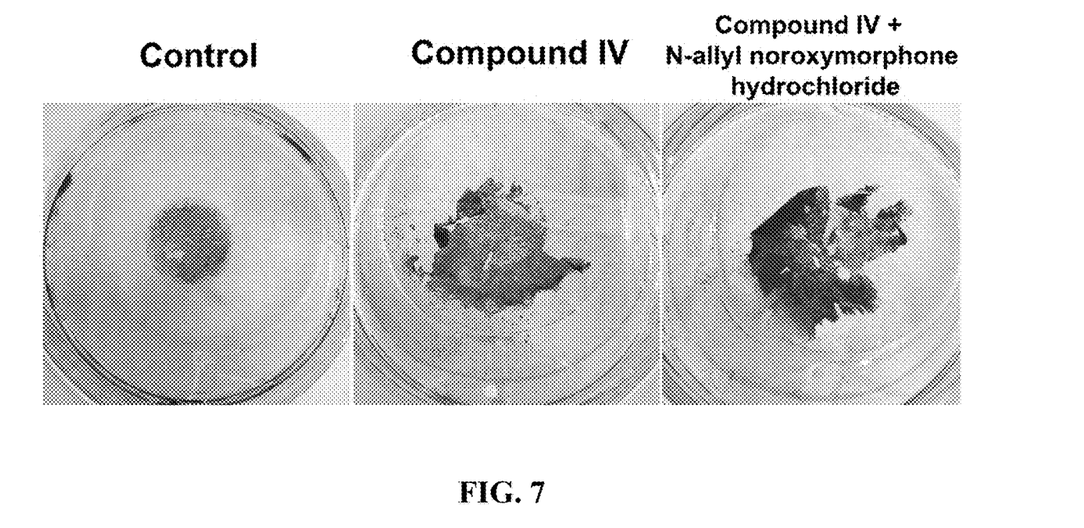
FIG. 7 shows mineral formation of the compound of Formula (IVa) in the presence and absence of N-allyl noroxymorphone hydrochloride in cultured mesenchymal stem cells.

The small molecule, N-allyl noroxymorphone hydrochloride, was added to Compound IVa ($SiH_3$—$[SiH_2]_n$—$SiH_2$—$[C_5H_7O_2]_n$ with $Ca_{10}(PO_4)_6(OH)_2$) at a concentration of 0.4-mg N-allyl noroxymorphone/mg of Compound IVa. Then the MAGE-Polymerization Initiator Solution containing the vinyl monomer vinyl methacrylate was added in a ratio of 2:1. The material—with or without N-allyl noroxymorphone hydrochloride—was then polymerized and added to cultures of mesenchymal stem cells (MSC), that were then assessed for the ability of the polymerized Compound IVa, with or without N-allyl noroxymorphone hydrochloride, to form bone mineral. Bone mineral formation was induced in control cultures (Control, FIG. 7) by supplementation beta-glycerophosphate, ascorbic acid, and dexamethasone. Cultures treated with Compound IVa, with or without N-allyl noroxymorphone hydrochloride, did not receive supplements to induce mineralization. The addition of Compound IVa, with or without N-allyl noroxymorphone hydrochloride, resulted in a significant increase in mineral formation (FIG. 7).

Example 4—Toxicity of the Compound (IVa) Polymer

The small molecule, N-allyl noroxymorphone hydrochloride, was added to Compound IVa ($SiH_3$—$[SiH_2]_n$—$SiH_2$—$[C_5H_7O_2]_n$ with $Ca_{10}(PO_4)_6(OH)_2$) at a concentration of 0.4-mg N-allyl noroxymorphone/mg of Compound IVa. Then the MAGE-Polymerization Initiator Solution containing the vinyl monomer vinyl methacrylate was added in a ratio of 2:1. The material—with N-allyl noroxymorphone hydrochloride—was then polymerized and added to cultures of BT-474 breast cancer cells. Cultures were also treated with N-allyl noroxymorphone hydrochloride alone. Control cultures received no treatment. In this example, relative to Control Cultures, the N-allyl noroxymorphone hydrochloride resulted a 59.7% decrease at 24-hours in cell number, and the Compound IVa with N-allyl noroxymorphone resulted in 62.1% decrease at 24-hours in cell number.

While certain embodiments have been illustrated and described, it should be understood that changes and modifications can be made therein in accordance with ordinary skill in the art without departing from the technology in its broader aspects.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of treating a bone injury or a bone condition comprising locally administering to a subject in need thereof at a bone injury site or a site affected by a bone condition an effective amount of a composition comprising a compound having a formula (IV):

wherein each of $R^1$, $R^2$, $R^3$, $R^4$, $R^5$, $R^6$, and $R^7$ is selected from the group consisting of H, alkyl, alkenyl, alkoxy, aryl, aralkyl, cycloalkyl, heterocyclyl, heteroaryl groups, hydroxyl, or halo, and n is independently for each occurrence an integer from 1 to 1000000.

2. The method of claim 1, wherein the composition further comprises N-allyl noroxymorphone hydrochloride.

3. The method of claim 1, wherein the compound has a formula (IVa):

4. The method of claim 1, wherein the composition further comprises an OGFR antagonist.

5. The method of claim 1, wherein n is 1 to 10,000.

6. The method of claim 1, wherein n is 1 to 100.

7. The method of claim 1, wherein the compound of formula (I) is prepared by a method comprising reacting methyl methacrylate with tetraethyl orthosilicate and 1,1,3,3-tetramethyldisilane.

8. The method of claim 7, wherein the tetraethyl orthosilicate and 1,1,3,3-tetramethyldisilane are reacted in a 0.375:0.375 volume ratio.

9. The method of claim 8, wherein 0.750-mL of the tetraethyl orthosilicate+1,1,3,3-tetramethyldisilane solution are added to 1-gram of polymethyl methacrylate is added.

10. The method of claim 1, wherein the compound is prepared by a method comprising reacting methyl methacrylate with tetraethyl orthosilicate and 1,1,3,3-tetramethyldisilane to form the $SiH_3$—$[SiH_2]_n$—$SiH_2$—$[C_5H_7O_2]_n$ wherein n is independently for each occurrence an integer from 1 to 1000000.

11. The method of claim 10, wherein the methyl methacrylate, tetraethyl orthosilicate, and 1,1,3,3-tetramethyldisilane are reacted for 12 to 18 hours at room temperature.

12. The method of claim 11, wherein addition of $Ca_{10}(PO_4)_6(OH)_2$ is performed by annealing with $SiH_3$—$[SiH_2]_n$—$SiH_2$—$[C_5H_7O_2]_n$.

* * * * *

UNITED STATES PATENT AND TRADEMARK OFFICE
CERTIFICATE OF CORRECTION

| | | |
|---|---|---|
| PATENT NO. | : 12,109,226 B1 | Page 1 of 1 |
| APPLICATION NO. | : 18/634556 | |
| DATED | : October 8, 2024 | |
| INVENTOR(S) | : Bryan S. Margulies | |

It is certified that error appears in the above-identified patent and that said Letters Patent is hereby corrected as shown below:

On the Title Page

Item (54) and In the Specification, Column 1, Line 1 in the TITLE, "POLYSILANE METHACRYLIC COMPOUNDS AND METHODS OF MAKING THEM" should be
-- POLYSILANE METHACRYLIC COMPOUNDS, METHODS OF MAKING THEM AND THEIR USES, INCLUDING FOR THE TREATMENT OF CANCER --

Signed and Sealed this
Eighteenth Day of February, 2025

Coke Morgan Stewart
*Acting Director of the United States Patent and Trademark Office*